United States Patent
Zagorchev et al.

(10) Patent No.: US 12,274,587 B2
(45) Date of Patent: Apr. 15, 2025

(54) METHOD FOR BONE COLLISION DETECTION USING A STEREOTACTIC IMAGE-GUIDED NAVIGATION SYSTEM

(71) Applicant: ClearPoint Neuro, Inc., Solana Beach, CA (US)

(72) Inventors: Lyubomir Zagorchev, Burlington, MA (US); Damon Hyde, Somerville, MA (US); Chen Li, Plainfield, OH (US); Philip Bradley Hotte, Solana Beach, CA (US); Timothy Neil Orr, Solana Beach, CA (US)

(73) Assignee: ClearPoint Neuro, Inc., Solana Beach, CA (US)

( * ) Notice: Subject to any disclaimer, the term of this patent is extended or adjusted under 35 U.S.C. 154(b) by 336 days.

(21) Appl. No.: 17/891,803

(22) Filed: Aug. 19, 2022

(65) Prior Publication Data
US 2024/0058088 A1   Feb. 22, 2024

(51) Int. Cl.
*G06T 17/20*   (2006.01)
*A61B 90/11*   (2016.01)

(52) U.S. Cl.
CPC ............. *A61B 90/11* (2016.02); *G06T 17/20* (2013.01); *G06T 2210/41* (2013.01)

(58) Field of Classification Search
None
See application file for complete search history.

(56) References Cited

U.S. PATENT DOCUMENTS

| | | | |
|---|---|---|---|
| 2012/0072183 A1* | 3/2012 | Lang | A61B 5/4514 703/1 |
| 2013/0035690 A1* | 2/2013 | Mittelstadt | G16H 50/50 382/128 |
| 2015/0366624 A1* | 12/2015 | Kostrzewski | A61B 90/11 606/130 |
| 2018/0360367 A1* | 12/2018 | Haesler | A61B 5/4064 |
| 2019/0209245 A1* | 7/2019 | Sparks | G06T 19/003 |

* cited by examiner

*Primary Examiner* — Sultana M Zalalee
(74) *Attorney, Agent, or Firm* — Sheppard Mullin Richter & Hampton LLP

(57) ABSTRACT

Systems and methods are provided that automatically determine whether a prospective surgical trajectory will collide with a patient's skull using a 3D representation of the patient's cranial region (including the patient's scalp, skull, and brain) adapted from imaging data of the patient's cranial region (e.g., MRI data or CT data). Taking a particular patient's varied skull thickness into account, examples can determine bone collision during a trajectory planning stage before or after a stereotactic frame is mounted to the patient. Accordingly, examples may preemptively alert a clinician to a potential bone collision before the prospective surgical trajectory is underway/has been executed, thereby reducing the risk of bone collision during the surgical procedure.

20 Claims, 11 Drawing Sheets

METHOD FOR BONE COLLISION DETECTION USING A STEREOTACTIC IMAGE-GUIDED NAVIGATION SYSTEM

TECHNICAL FIELD

The present disclosure relates generally to medical technologies, and more particularly, some examples relate to detecting bone collision during surgical procedures.

BACKGROUND

Stereotactic frames mounted to a patient's skull or scalp can be used to guide a surgical instrument along a linear (or approximately linear) trajectory to a target brain region during brain surgeries. In particular, the surgical instrument may be inserted through, and guided by, a targeting cannula of the stereotactic frame. Before advancing/guiding the surgical instrument into the patient's brain, the targeting cannula typically guides the surgical instrument through a cylindrical hole drilled into a patient's skull (e.g., a burr hole). The distal tip of the targeting cannula (through which the surgical instrument is inserted) and an angulation of the targeting cannula can define the trajectory the surgical instrument is guided along. During surgeries, the distal tip of the targeting cannula typically remains located at or above the exterior surface of the patient's skull—while the surgical instrument inserted through the targeting cannula advances into the patient's skull/brain.

In general, the thickness of a patient's skull will vary along the patient's skull. In other words, the distance between the exterior surface of the patient's skull and the interior surface of the patient's skull (i.e., the brain-facing surface) will vary along the patient's skull. As will be described in greater detail below, such varied skull thickness can cause complications when planning and/or executing surgical trajectories through a patient's skull.

BRIEF DESCRIPTION OF THE DRAWINGS

The present disclosure, in accordance with one or more various examples, is described in detail with reference to the following figures. The figures are provided for purposes of illustration only and merely depict examples.

Figure 1:
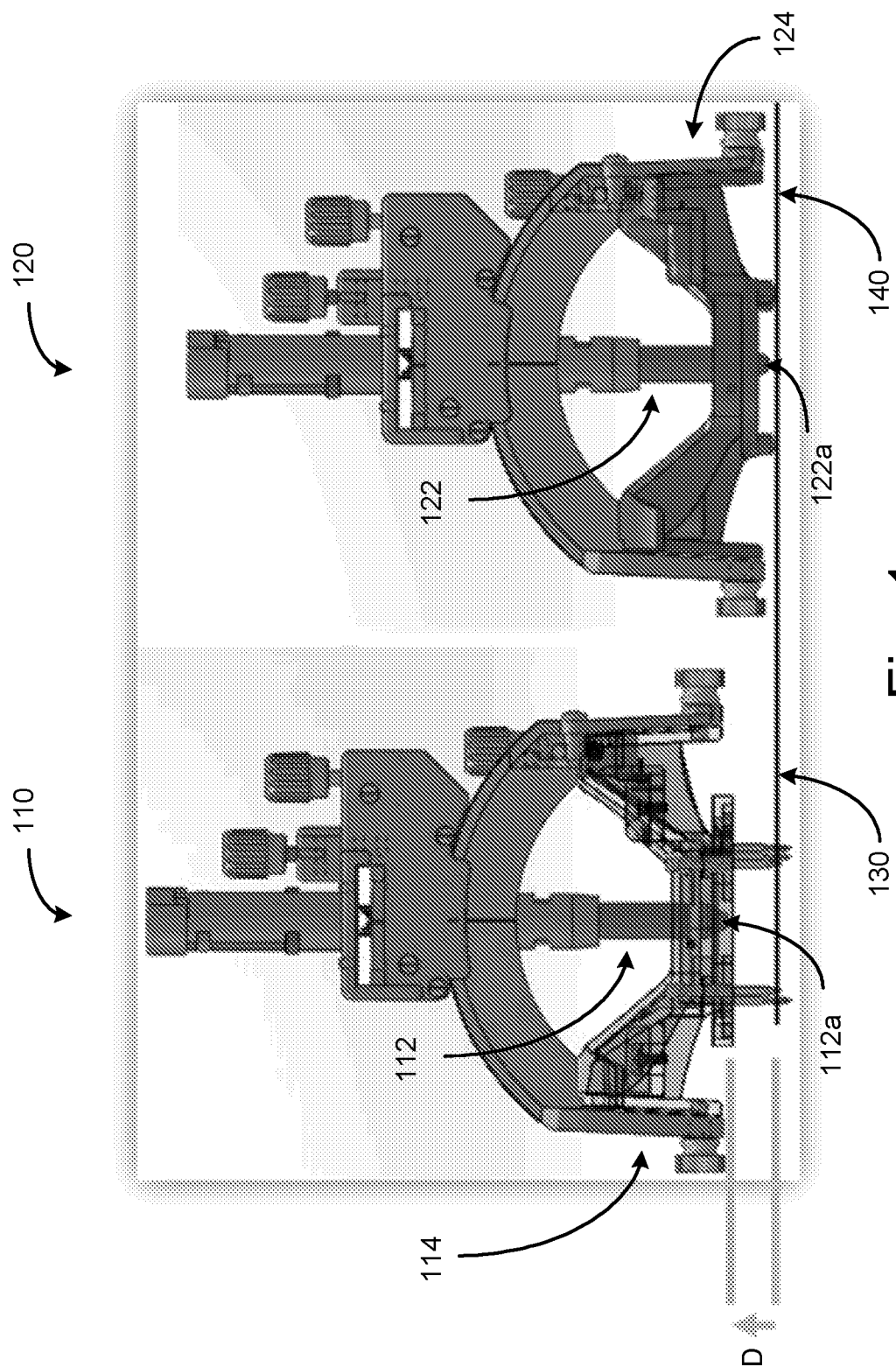
FIG. 1 depicts an example scalp-mounted stereotactic frame and an example skull-mounted stereotactic frame, in accordance with various examples of the presently disclosed technology.

The figures are not exhaustive and do not limit the present disclosure to the precise form disclosed.

DETAILED DESCRIPTION

As described above, during brain surgeries, targeting cannulas of stereotactic frames (see e.g., FIG. 1) mounted to a patient's skull or scalp can be used to guide a surgical instrument along a linear (or approximately linear) trajectory to a target brain region. Before advancing/guiding the surgical instrument into the patient's brain, the targeting cannula may guide the surgical instrument through a cylindrical hole drilled into a patient's skull (e.g., a burr hole). The cylindrical hole for the above described surgical procedures will span a distance/thickness between the exterior surface of the patient's skull and the interior surface of the patient's skull.

During the surgical procedures described above, it is important to avoid collision between the inserted surgical instrument and the patient's skull (i.e., bone collisions). Such bone collisions can arise when extreme-angled surgical trajectories are followed through a cylindrical hole in the patient's skull. In other words, if a surgical instrument inserted through the cylindrical hole follows a trajectory set forth by the targeting cannula/stereotactic frame such that the surgical instrument is "guided" into actual bone, problems can occur. The problems that result from such collisions should be avoided because they can cause patient trauma (by e.g., deflection of the surgical instrument into the patient's brain), and in many cases require remounting of the stereotactic frame which can undesirably extend the time needed to perform a surgical procedure, and cause additional trauma for the patient. Delays caused by bone collision can be even more harmful in surgical procedures conducted under computerized tomography (CT) guidance because longer procedures expose the patient to additional radiation (here unexpected bone collision is still a risk for surgical procedures conducted under CT/MRI guidance because bone cannot always be accurately visualized using CT/MRI).

As described above, a patient's skull varies in thickness depending on skull location/area. Accordingly, an extreme-angled surgical trajectory may result in bone collision when followed through a cylindrical hole in a patient's skull at a first location (e.g., a thicker area/location of the patient's skull), where the same extreme-angled surgical trajectory may not result in bone collision when followed through a cylindrical hole in the patient's skull at a second location (e.g., a thinner area/location of the patient's skull). In other words, the range of "safe" surgical trajectory angles typically varies based on skull location because skull thickness varies based on skull location. Generally lacking reliable and reproducible techniques for estimating skull thickness at prospective entry points for entering a patient's skull, the above described variability raises challenges for existing surgical trajectory planning systems.

Against this backdrop, examples of the presently disclosed technology provide computerized surgical trajectory planning systems that automatically predict whether a prospective surgical trajectory will collide with a patient's skull (sometimes referred to as "bone collision") using a 3D representation of the patient's cranial region (including the patient's scalp, skull, and brain), adapted from imaging data of the patient's cranial region (e.g., MRI data or CT data). Taking a particular patient's varied skull thickness into account, examples can determine bone collision during a trajectory planning stage before or after a stereotactic frame is mounted to the patient. Accordingly, examples may pre-emptively alert a clinician to a potential bone collision before the prospective surgical trajectory is underway/has been executed, thereby reducing the risk of bone collision during the surgical procedure.

Examples can predict or determine the possibility of a bone collision for a prospective surgical trajectory by: (1) computing a surface normal to a given exterior skull surface location of a patient using a 3D representation of the patient's cranial region adapted from imaging data of the patient's cranial region, the given exterior skull surface location being a prospective entry point for entering the patient's skull through a prospective cylindrical hole having a given radius and a longitudinal axis along the computed surface normal to the given exterior skull surface location; (2) computing a thickness of the patient's skull along a downwards projection of the computed surface normal using the 3D representation; and (3) predicting, based on the computed thickness and the given radius of the prospective cylindrical hole, whether a prospective trajectory for inserting a surgical instrument through the prospective cylindrical hole will collide with the patient's skull, the prospective trajectory originating at the given exterior skull surface location. Each step in this process will be described in greater detail in the following paragraphs.

As described above, examples may compute a surface normal to a given exterior skull surface location of a patient (i.e., a vector perpendicular to the patient's exterior skull surface at the given exterior skull surface location) using a 3D representation of the patient's cranial region (i.e., a 3D representation of the patient's scalp, skull, and brain) adapted from imaging data of the patient's cranial region (e.g., MRI data or CT data). The given exterior skull surface location may be a prospective entry point for entering the patient's skull through a prospective cylindrical hole having a given radius and a longitudinal axis along the computed surface normal. The 3D representation of the patient's cranial region may include an exterior skull mesh boundary surface that represents the exterior surface of the patient's skull and an interior skull mesh boundary surface that represents the interior surface of the patient's skull (here the 3D representation may represent the patient's brain and scalp as well). The exterior and interior skull mesh boundary surfaces may be comprised of mesh elements and mesh vertices.

Examples can compute the surface normal to the given exterior skull surface location using the exterior skull mesh boundary surface. For instance, examples can compute an average of surface normals for one or more mesh elements in close proximity to a location on the exterior skull mesh boundary surface corresponding to the given exterior skull surface location. Alternatively, examples may compute the surface normal to the given exterior skull surface location by performing principal component analysis on one or more mesh vertices in close proximity to the location on the exterior skull mesh boundary surface corresponding to the given exterior skull surface location.

Once examples have computed the surface normal to the given exterior skull surface location, a thickness of the patient's skull may be computed along a downwards projection from the computed surface normal using the 3D representation. In various examples, this may comprise computing a distance between the location on the exterior skull mesh boundary surface corresponding to the given exterior skull surface location and a location on the interior skull mesh boundary surface that intersects the downwards projection from the computed surface normal.

Based on (a) the computed thickness of the patient's skull (which again can vary based on location, and which is not typically a consideration for existing surgical trajectory planning systems); and (b) the given radius of the prospective cylindrical hole, examples may predict whether a prospective trajectory for inserting a surgical instrument through the prospective cylindrical hole will collide with the patient's skull. Here, the prospective trajectory may originate at the given exterior skull surface location. In various examples, the prediction may comprise (1) computing, based on the computed thickness of the patient's skull and the given radius of the prospective cylindrical hole, a maximum acceptable angle for inserting the surgical instrument through the prospective cylindrical hole such that the surgical instrument does not collide with the patient's skull, the maximum acceptable angle having a vertex at the given exterior skull surface location; and (2) predicting that the prospective trajectory creates a prospective trajectory angle that exceeds the maximum acceptable angle, the prospective trajectory angle having a vertex at the given exterior skull surface location.

In various examples, upon predicting that the prospective trajectory will collide with the patient's skull, examples may provide an alert to a clinician, or in certain instances, propose a new trajectory with a new prospective entry point for entering the patient's skull.

As described above, examples may predict bone collision during a trajectory planning stage before and/or after a stereotactic frame is mounted to the patient. For example, where a stereotactic frame has already been mounted to the patient, examples may predict whether a prospective trajectory will collide with the patient's skull by: (1) detecting a location of a distal tip of a targeting cannula of the stereotactic frame mounted to the patient's cranial region; (2) computing a surface normal to the patient's skull at the distal tip of the targeting cannula using a 3D representation of the patient's cranial region adapted from imaging data of the patient's cranial region; (3) computing a thickness of the patient's skull along a downwards projection from the computed surface normal using the 3D representation; and (4) predicting that a prospective trajectory for inserting a surgical device through a cylindrical hole in the patient's skull will collide with the patient's skull, the prospective trajectory originating at the distal tip of the targeting cannula, the cylindrical hole having a given radius and a longitudinal axis along the computed surface normal, wherein the predicting is based on: (a) the computed thickness of the patient's skull; and (b) the given radius of the cylindrical hole. Each step in this process will be described in greater detail in the following paragraphs.

As described above, examples may detect a location of a distal tip of a targeting cannula of a stereotactic frame mounted to a patient's cranial region. In various instances, examples may utilize imaging data from the surgical procedure to make this detection.

In some instances, examples may also detect an angulation of the targeting cannula (by e.g., examining imagining data of the surgical procedure). Here, based on the detected location of the distal tip and the detected angulation for the targeting cannula, examples may predict/anticipate the prospective trajectory (as described above, a surgical trajectory can be thought of as originating at the distal tip of the targeting cannula, and proceeding linearly at the angulation of the targeting cannula).

After detecting the location of the distal tip of the targeting cannula, examples may compute a surface normal to the patient's skull at the distal tip of the targeting cannula using a 3D representation of the patient's cranial region adapted from imaging data of the patient's cranial region. As described above, the 3D representation may comprise an exterior skull mesh boundary surface that represents the exterior surface of the patient's skull and an interior skull mesh boundary surface that represents the interior surface of the patient's skull. In various examples, computing the surface normal to the patient's skull at the distal tip of the targeting cannula may comprise (1) determining a location on the exterior skull mesh boundary surface that corresponds to the distal tip of the targeting cannula; and (2) either (a) computing an average of surface normals for one or more mesh elements in close proximity to the determined location on the exterior skull mesh boundary surface corresponding to the distal tip of the targeting cannula; or (b) performing principal component analysis on one or more mesh vertices in close proximity to the location on the exterior skull mesh boundary surface corresponding to the distal tip of the targeting cannula.

Examples may determine the location on the exterior skull mesh boundary surface corresponding to the distal tip of the targeting cannula in various ways depending on whether the stereotactic frame is mounted to the patient's skull (i.e., a skull mount) or scalp (i.e., a scalp mount). Where the stereotactic frame is mounted to the patient's skull, the distal tip of the targeting cannula may be positioned (approximately) at the exterior surface of the patient's skull. Accordingly, the location on the exterior skull mesh boundary surface that corresponds to the distal tip of the targeting cannula may be the location on the exterior skull mesh boundary surface that corresponds to the location on the exterior surface of the patient's skull at which the distal tip of the targeting cannula is positioned. By contrast, where the stereotactic frame is mounted to the patient's scalp, the distal tip of the targeting cannula may be positioned above the exterior surface of the patient's skull by a vertical distance (i.e., a vertical offset). To account for the vertical offset of scalp-mounted stereotactic frames, examples may determine the location on the exterior skull mesh boundary surface that corresponds to the distal tip of the targeting cannula by (1) determining a vertical distance that the distal tip of the targeting cannula is located above the exterior surface of the patient's skull; and (2) projecting the exterior skull mesh boundary surface vertically upwards by the determined vertical distance such that the projection of the exterior skull mesh boundary surface intersects the distal tip of the targeting cannula; and (3) based on the projection, determining the location on the exterior skull mesh boundary surface that corresponds to the distal tip of the targeting cannula.

With the surface normal computed, examples may compute a thickness of the patient's skull along a downwards projection from the surface normal using the 3D representation. In various examples, this may comprise computing a distance between the location on the exterior skull mesh boundary surface corresponding to the distal tip of the targeting cannula and a location on the interior skull mesh boundary surface that intersects the downwards projection of the computed surface normal.

After computing the thickness of the patient's skull along the surface normal, examples may predict whether a prospective trajectory for inserting a surgical instrument through a cylindrical hole in the patient's skull will collide with the patient's skull. The prospective trajectory may originate at the distal tip of the targeting cannula, and follow the angulation of the targeting cannula. As described above, in certain instances, examples may predict the prospective trajectory based on the detected location of the distal tip and a detected angulation of the targeting cannula.

The cylindrical hole may have a given radius and a longitudinal axis along the computed surface normal. The cylindrical hole may be a prospective cylindrical hole or a cylindrical hole that has already been drilled/burred into the patient's skull.

The predicting may be based on: (a) the computed thickness of the patient's skull; and (b) the given radius of the cylindrical hole. In various instances, predicting whether the prospective trajectory for inserting the surgical instrument through the cylindrical hole will collide with the patient's skull may comprise: (1) computing a maximum acceptable angle for inserting the surgical instrument through the cylindrical hole such that the surgical instrument does not collide with the patient's skull, the maximum acceptable angle having a vertex at the distal tip of the targeting cannula, the computation of the maximum acceptable angle being based on: (a) the computed thickness of the patient's skull, (b) the determined vertical distance that the distal tip of the targeting cannula is located above the exterior surface of the patient's skull, and (c) the radius of the cylindrical hole; and (2) predicting that the prospective trajectory creates a prospective trajectory angle that exceeds the maximum acceptable angle, the prospective trajectory angle having a vertex at the distal tip of the targeting cannula.

Where the stereotactic frame is mounted to the patient's skull (i.e., where there is no vertical offset between the distal tip of the targeting cannula and exterior skull surface of the patient), examples may compute the maximum acceptable angle as follows where "α" is the maximum acceptable angle:

$$\tan(\alpha) = \frac{\text{cylindrical hole radius}}{\text{computed skull thickness}}$$

Where the stereotactic frame is mounted to the patient's scalp (i.e., where there is a vertical offset between the distal tip of the targeting cannula and the exterior skull surface of the patient), examples may compute the maximum acceptable angle as follows where "α" is the maximum acceptable angle and the "distal tip offset" is the determined vertical distance between the distal tip of the targeting cannula and the patient's exterior skull surface (in some cases, this vertical distance may be approximately the thickness of the patient's scalp beneath the distal tip of the targeting cannula):

$$\tan(\alpha) = \frac{\text{cylindrical hole radius}}{\text{computed skull thickness} + \text{distal tip offset}}$$

Utilizing the techniques described above, examples can provide computerized surgical trajectory planning systems with enhanced bone collision prediction capabilities. As described above, examples may predict that prospective trajectories will collide with a patient's skull before and after a stereotactic frame has been mounted to a patient.

Where examples predict bone collision for a prospective trajectory before a stereotactic frame is mounted to a patient, examples may not only provide an alert to a user/clinician regarding the predicted bone collision, but also assist a user/clinician by recommending, e.g., a new stereotactic frame mounting location, a new skull entry point, a new trajectory, etc.—that will not result in bone collision. For instance, if examples predict bone collision based on a trajectory for a first prospective stereotactic frame mounting location, examples may recommend a second prospective stereotactic frame mounting location which would allow for a trajectory (having a less extreme angle) that can reach the same target brain region without colliding with the patient's skull.

Where examples predict bone collision for a prospective trajectory after a stereotactic frame is mounted to a patient, examples may also assist a user/clinician by not only providing an alert but recommending, e.g., a new stereotactic frame mounting location, an adjusted distal tip location for the targeting cannula, an adjusted angulation for the targeting cannula, etc.—that will not result in bone collision. In many cases, the location of the distal tip of the targeting cannula can be adjusted without re-mounting the stereotactic frame to the patient. The angulation of the targeting cannula can be adjusted without frame re-mounting as well. Accordingly, examples may predict that a trajectory for a first location of the distal tip and a first angulation of the targeting cannula will result in bone collision. Based on this prediction, examples may recommend an adjusted position of the distal tip and an adjusted angulation of the targeting cannula to achieve a less extreme angled trajectory that does not collide with the patient's skull. Such a trajectory may be achieved without re-mounting the stereotactic frame to the patient, thereby reducing patient trauma and reducing surgical intervention time (which may also reduce patient trauma).

As described above, by providing computerized surgical trajectory planning systems that can predict and prevent bone collisions before they happen, examples of the presently disclosed technology may improve patient safety. Such safety improvement may be realized by avoiding bone collisions during surgical procedures, but also by reducing surgical intervention times. In other words, by facilitating safe, pre-planned trajectories, examples may reduce surgical intervention times, thereby increasing patient comfort, and in some cases, reducing a patient's exposure to harmful radiation.

The benefits of the presently disclosed technology may also extend beyond bone collision detection. For instance, examples can provide improved techniques for computing patient skull thicknesses (i.e., by utilizing 3D mesh representations of the patient's skull adapted from imaging data of the patient's cranial region). These techniques may compute skull thicknesses more accurately (or less intrusively) than existing techniques for computing/estimating skull thicknesses. Relatedly, examples may utilize the same/similar techniques (i.e., utilizing 3D mesh representations of the patient's scalp adapted from imaging data of the patient's cranial region) to compute patient scalp thicknesses more accurately than existing techniques for computing scalp thicknesses. Accordingly, examples of the presently disclosed technology may enhance computerized systems used to compute skull and scalp thicknesses for patients.

Examples of the presently disclosed technology may leverage the improved skull and scalp thickness computations described above in various ways. For instance, examples may leverage skull and scalp thickness computations to refine sizing and selection for screws that are inserted into a patient's skull and/or scalp for various medical procedures. As a more specific example related to scalp-mounted stereotactic frames, examples may leverage accurate scalp thickness computations to refine mounting screw locations and improve estimates of vertical offsets between a patient's skull and the distal tip of the targeting cannula.

FIG. 1 depicts an example scalp-mounted stereotactic frame 110 and an example skull-mounted stereotactic frame 120, in accordance with various examples of the presently disclosed technology. As depicted, each stereotactic frame comprises a targeting cannula (i.e., targeting cannulas 112 and 122), and a mounting base (i.e., mounting bases 114 and 124) for mounting the stereotactic frame to a patient's cranial region.

As described above, during brain surgeries, targeting cannulas (e.g., targeting cannulas 112 and 122) of stereotactic frames are used to guide a surgical instrument along a linear (or approximately linear) trajectory to a target brain region. In particular, the surgical instrument is inserted through a distal tip of the targeting cannula, and advanced through the patient's cranial region along an approximately linear trajectory defined by an angulation of the targeting cannula.

In general, two types of stereotactic frames are used in the surgical procedures described above: scalp-mounted stereotactic frames comprising mounting bases that affix the scalp-mounted stereotactic frame to a patient's scalp; and skull-mounted stereotactic frames comprising mounting bases that affix the skull-mounted stereotactic frame to a patient's skull. An advantage of a scalp-mounted stereotactic frame such as scalp-mounted stereotactic frame 110 is that it requires minimal scalp incision, and accordingly may reduce patient trauma. A skull-mounted stereotactic frame such as skull-mounted stereotactic frame 120 requires a larger scalp incision, but keeps the stereotactic frame closer to the patient's skull.

As depicted in FIG. 1, the distal tip of a targeting cannula (i.e. distal tip 122a) for skull-mounted stereotactic frame 120 may be located approximately at the exterior surface of a patient's skull (i.e., exterior skull surface 140). By contrast, the distal tip of a targeting cannula (i.e. distal tip 112a) for scalp-mounted stereotactic frame 110 may be located a vertical distance (D) above the exterior surface of a patient's skull (i.e., exterior skull surface 130). This distance (D) may be approximately the thickness of the patient's scalp between distal tip 112a and exterior skull surface 130. As described above, and as will be described in greater detail below, when predicting bone collision for a prospective surgical trajectory, examples of the presently disclosed technology may account for the vertical distance between distal tip 112a and exterior skull surface 130 by determining a location on an exterior skull mesh boundary surface representing exterior skull surface 130 that corresponds to distal tip 112a. Examples may make this determination by (1) determining the vertical distance (D) that distal tip 112a is located above exterior skull surface 130; (2) projecting the exterior skull mesh boundary surface vertically upwards by the determined vertical distance (D) such that the projection of the exterior skull mesh boundary surface intersects distal tip 112a; and (3) based on the projection, determining the location on the exterior skull mesh boundary surface that corresponds to distal tip 112a.

Figure 2:
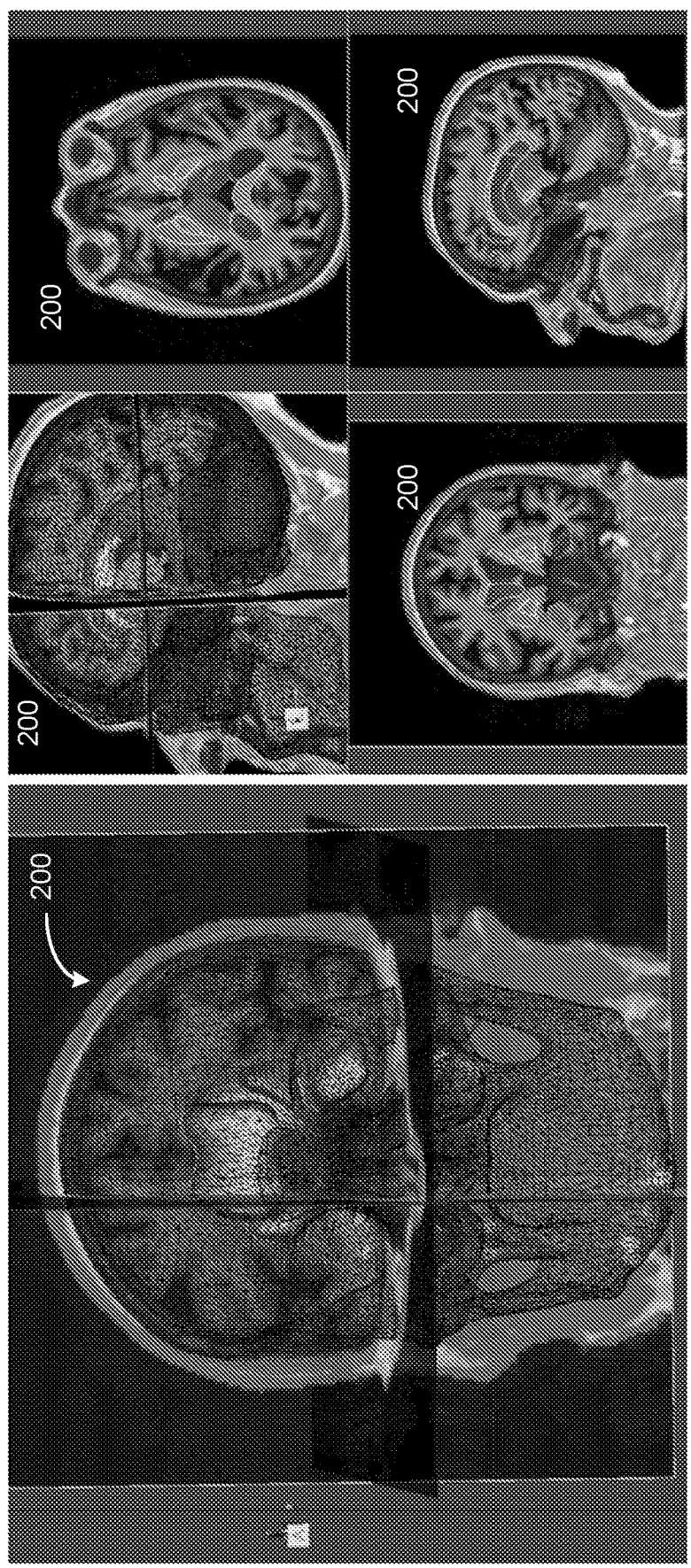
FIG. 2 depicts a series of perspective views of an example 3D representation of a patient's cranial region, in accordance with various examples of the presently disclosed technology.

FIG. 2 depicts five perspective views of an example 3D representation 200 of a patient's cranial region (as used herein, a patient's cranial region may refer to the patient's scalp, skull, and brain), in accordance with various examples of the presently disclosed technology. As described above, 3D representation 200 may be a 3D representation of the patient's cranial region adapted from imaging data of the patient's cranial region (e.g., MRI data or CT data). As depicted, 3D representation 200 may utilize meshes/surface meshes to represent the patient's cranial region.

As described above, a mesh or surface mesh may refer to a representation of a larger domain (e.g., a volume or surface) comprised of smaller discrete cells called mesh elements (here, mesh vertices may be at the junctions of adjacent/adjoining mesh elements). Meshes can be used to compute solutions to equations across individual mesh elements, which then can be used to approximate solutions over the larger domain.

As depicted, 3D representation 200 contains surface meshes representing: (1) the exterior scalp surface of the patient (i.e., an exterior scalp mesh boundary surface); (2) the interior scalp surface of the patient (i.e., an interior scalp mesh boundary surface); (3) the exterior skull surface of the patient (i.e., an exterior skull mesh boundary surface); and (4) the interior skull surface of the patient (i.e., an interior skull mesh boundary surface). Each mesh boundary surface may be comprised of mesh elements and mesh vertices at the junctions of adjoining mesh elements. As depicted, the mesh elements comprise mesh triangles, but in other examples the mesh elements may comprise different shapes.

As described above, and as will be described in greater detail below, 3D representations such as 3D representation 200 may be used to (1) compute skull and/or scalp surface normals; 2) estimate skull and/or scalp thicknesses along downwards projections from the computed surface normals; and 3) detect bone collision for a prospective trajectory based on the computed skull/scalp thicknesses.

Figure 3:
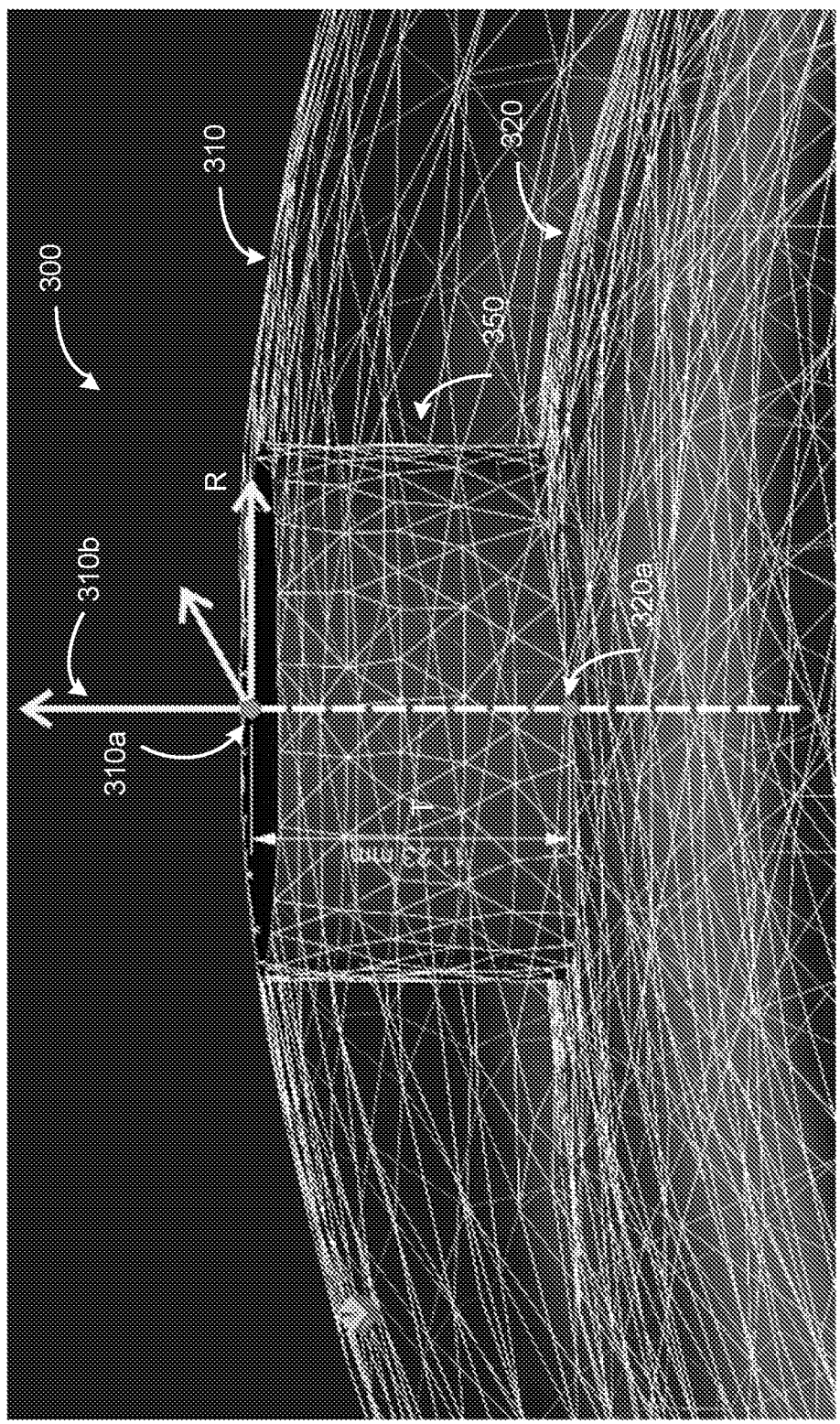
FIG. 3 depicts an example 3D representation of a patient's cranial region, in accordance with various examples of the presently disclosed technology.

FIG. 3 depicts an example 3D representation 300 of a patient's cranial region, in accordance with various examples of the presently disclosed technology. 3D representation 300 may be a 3D representation of the patient's cranial region adapted from imaging data (e.g., MRI data or CT data) of the patient's cranial region.

3D representation 300 contains two surface meshes: (1) exterior skull mesh boundary surface 310 which represents the patient's exterior skull surface; and (2) interior skull mesh boundary surface 320 which represents the patient's interior skull surface. 3D representation 300 also includes a given exterior skull mesh boundary surface location 310a which represents a given exterior skull surface location on the patient's skull. The given exterior skull surface location may be a prospective entry point for entering the patient's skull through a cylindrical hole in the patient's skull. As will be described below, this cylindrical hole may have a longitudinal axis along a computed surface normal to the given exterior skull surface location (i.e., computed surface normal 310b).

Examples of the presently disclosed technology may compute skull thickness at the given exterior skull surface location by first computing a surface normal to the given exterior skull surface location (i.e., computed surface normal 310b) using 3D representation 300 (as used herein, a surface normal to the given exterior skull surface location may refer to a vector originating at the given exterior skull surface location which is perpendicular to the patient's exterior skull surface at the given exterior skull surface location). Examples may accomplish this surface normal computation using various techniques. For instance, examples may compute surface normal 310b by computing an average of surface normals for one or more mesh elements in close proximity to given exterior skull mesh boundary surface location 310a (here a computed surface normal for given exterior skull mesh boundary surface location 310a may closely approximate the actual surface normal to the given exterior skull surface location as given exterior skull mesh boundary surface location 310a represents the given exterior skull surface location on exterior skull mesh boundary surface 310). Alternatively, examples may compute surface normal 310b by performing principal component analysis on one or more mesh vertices in close proximity to given exterior skull mesh boundary surface location 310a.

Using computed surface normal 310b, examples may compute the thickness of the patient's skull at the given exterior skull surface location by computing a distance between given exterior skull mesh boundary surface location 310a and a location on interior skull mesh boundary surface 320 that intersects a downwards projection of computed surface normal 310b (i.e., interior skull mesh boundary surface location 320a). Examples may leverage this computed skull thickness for various purposes, including for predicting whether a prospective trajectory for inserting a surgical instrument through a cylindrical hole in the patient's skull, will collide with the patient's skull.

As described above, the given exterior skull surface location may be a prospective entry point for entering the patient's skull through a cylindrical hole in the patient's skull. Accordingly, FIG. 3 also depicts a visualized cylindrical hole 350. Visualized cylindrical hole 350 may be a 3D representation of an actual or prospective cylindrical hole in the patient's skull. Visualized cylindrical hole 350 has a first opening at exterior skull mesh boundary surface 310, a second opening at interior skull mesh boundary surface 320, and a longitudinal axis along computed surface normal 310b. Visualized cylindrical hole 350 also has a radius (R) and a height/thickness (T). Here, the thickness (T) of visualized cylindrical hole 350 may be the computed thickness of the patient's skull at the given exterior skull surface location. As will be described in greater detail in conjunction with FIG. 4, examples may predict whether a prospective trajectory for inserting a surgical instrument through a cylindrical hole in the patient's skull (represented by visualized cylindrical hole 350), will collide with the patient's skull.

Figure 4:
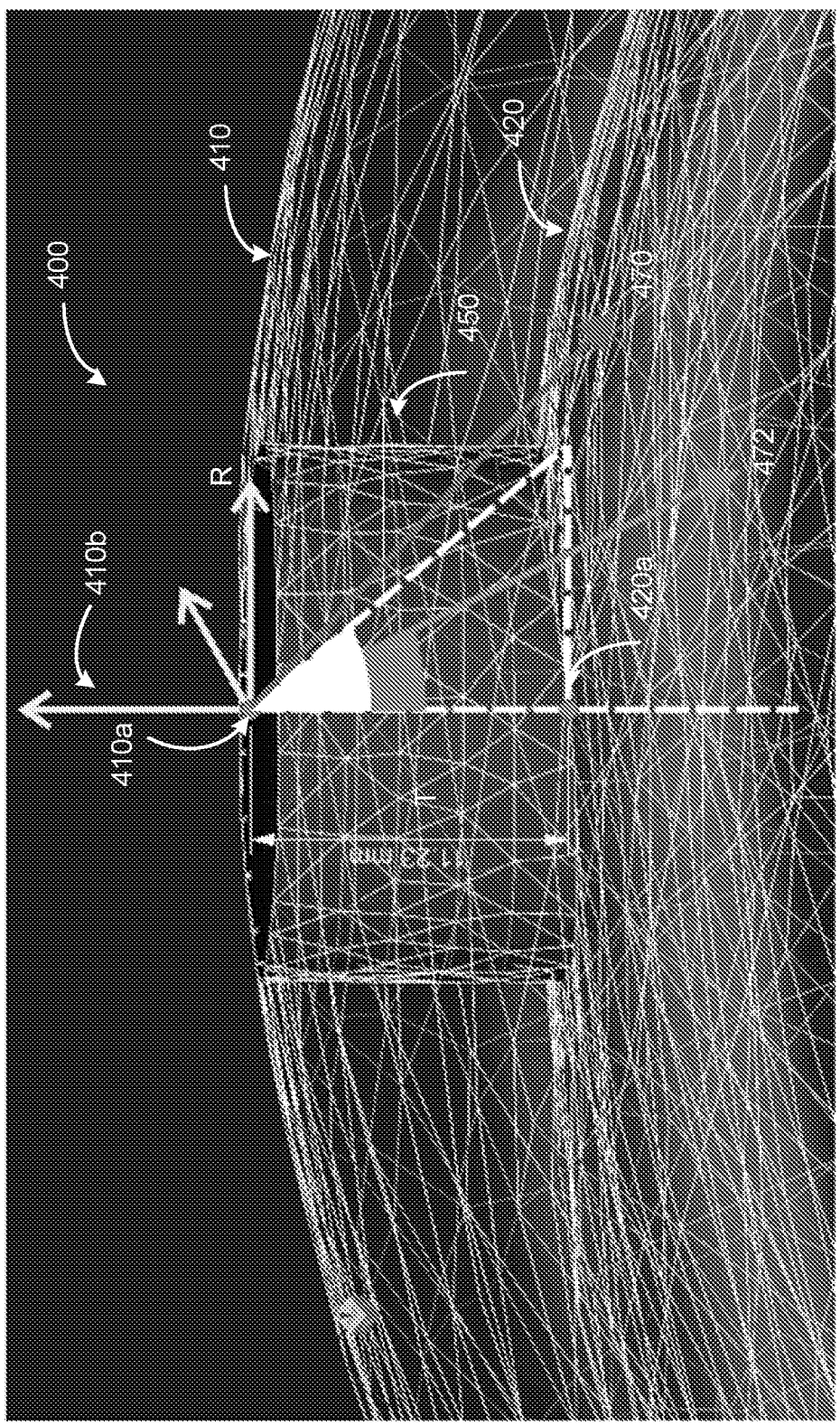
FIG. 4 depicts another example 3D representation of a patient's cranial region, in accordance with various examples of the presently disclosed technology.

Before proceeding to FIG. 4, it should be understood that the techniques described in conjunction with FIG. 3 may be extended for computing surface normals and thicknesses for a patient's scalp. For example, exterior skull mesh boundary surface 310 may instead represent the patient's exterior scalp surface, interior skull mesh boundary surface 320 may instead represent the patient's interior scalp surface, and given exterior skull mesh boundary surface location 310a may instead represent a given exterior scalp surface location. Accordingly, examples may compute a surface normal and scalp thickness at the given exterior scalp surface location using the same/similar techniques described above.

FIG. 4 depicts an example 3D representation 400 of a patient's cranial region, in accordance with various examples of the presently disclosed technology. 3D representation 400 may be the same/similar as 3D representation 300 from FIG. 3. Accordingly, components of FIG. 4 having reference numbers corresponding to component reference numbers of components introduced and described above with respect to FIG. 3 may have similar functionality and aspects.

As alluded to above, given exterior skull mesh boundary surface location 410a may represent a given exterior skull surface location on the patient's skull. The given exterior skull surface location may be a prospective entry point for entering the patient's skull through a cylindrical hole in the patient's skull represented by visualized cylindrical hole 450. As described above, visualized cylindrical hole 450 may have a longitudinal axis along a computed surface normal to the given exterior skull surface location (i.e., computed surface normal 410b). Visualized cylindrical hole 450 may also have a radius (R) and a height/thickness (T). Here, the thickness (T) of visualized cylindrical hole 450 may be a computed thickness of the patient's skull at the given exterior skull surface location (i.e., the computed thickness of the patient's skull along a downwards projection from computed surface normal 410b).

As described above, based on the computed thickness (T) of visualized cylindrical hole 450 and the radius (R) of visualized cylindrical hole 450, examples may predict whether a prospective trajectory for inserting a surgical instrument through the cylindrical hole represented by visualized cylindrical hole 450 will collide with the patient's skull, the prospective trajectory originating at the given exterior skull location represented by given exterior skull mesh boundary surface location 410a. In various examples, this prediction may comprise (1) computing a maximum acceptable angle for inserting the surgical instrument through the cylindrical hole such that the surgical instrument does not collide with the patient's skull, the maximum acceptable angle having a vertex at the given exterior skull surface location (represented by given exterior skull mesh boundary surface location 410a); and (2) predicting whether the prospective trajectory creates a prospective trajectory angle that exceeds the maximum acceptable angle.

Examples may calculate the maximum acceptable angle using the following equation, where a is the maximum acceptable angle, T is the computed thickness of visualized cylindrical hole 450, and R is the radius of visualized cylindrical hole 450:

$$\tan(\alpha) = \frac{R}{T}$$

Here, examples may predict that prospective trajectories that create prospective trajectory angles which exceed the maximum acceptable angle α will collide with the patient's skull. For instance, examples may predict that prospective trajectory 470 will collide with the patient's skull as the prospective trajectory angle for prospective trajectory 470 exceeds the maximum acceptable angle α. By contrast, examples may predict that prospective trajectory 472 will not collide with the patient's skull as the prospective trajectory angle for prospective trajectory 472 does not exceed the maximum acceptable angle α.

Figure 5:
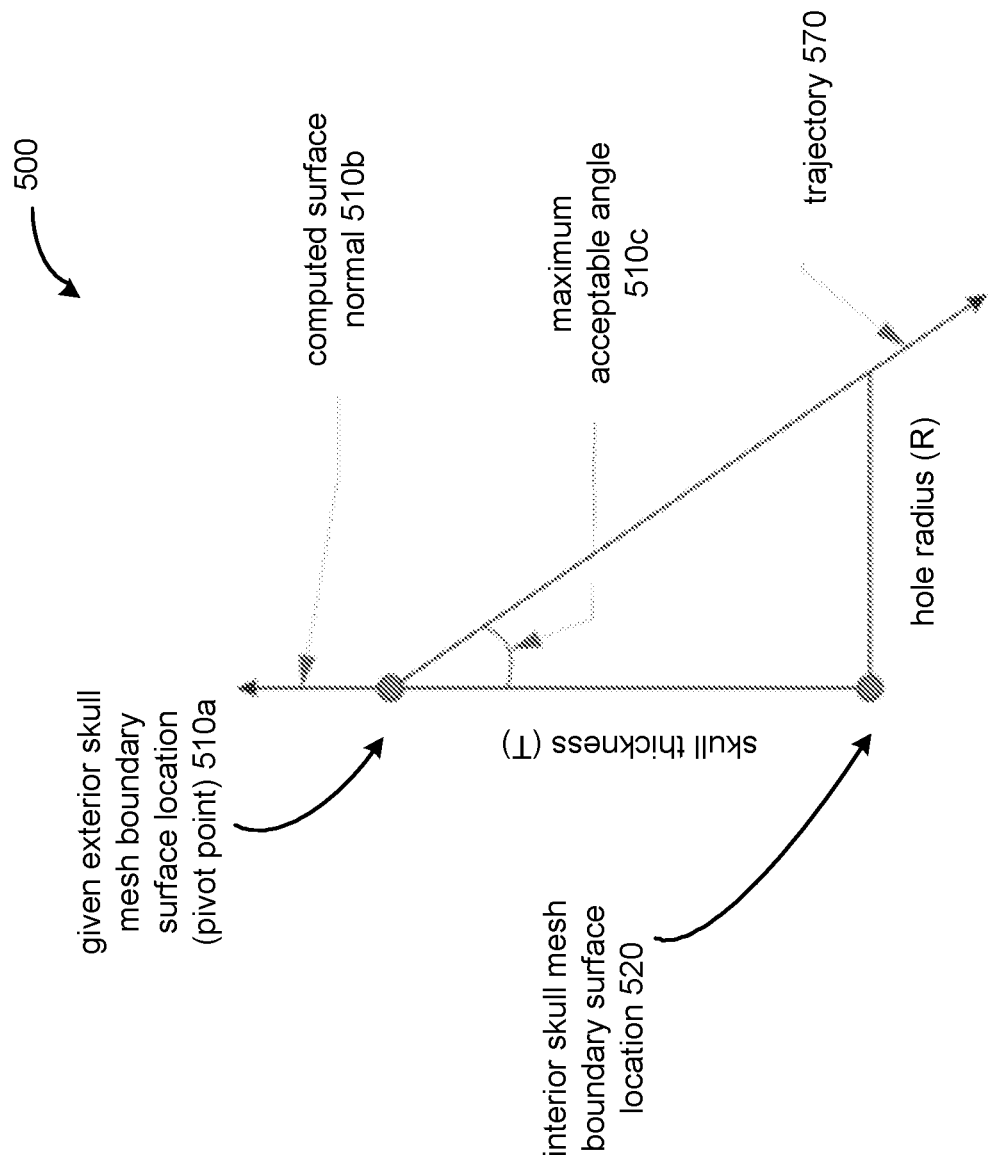
FIG. 5 contains a diagram that depicts how a maximum acceptable angle that avoids bone collision may be computed for a skull-mounted stereotactic frame, in accordance with various examples of the presently disclosed technology.

FIG. 5 contains a diagram 500 that depicts how a maximum acceptable angle 510c that avoids bone collision may be computed for a skull-mounted stereotactic frame, in accordance with various examples of the presently disclosed technology. Components of FIG. 5 having reference numbers corresponding to component reference numbers of components introduced and described above with respect to FIGS. 3 and 4 may have similar functionality and aspects.

Referring now to diagram 500, given exterior skull mesh boundary surface location 510a may represent a given exterior skull surface location on the patient's skull. The given exterior skull surface location may be a prospective entry point for entering the patient's skull through a cylindrical hole (actual or prospective) having a longitudinal axis along computed surface normal 510b. As described above, the distal tip of the targeting cannula for the skull-mounted stereotactic frame may be located approximately at the given exterior skull surface location (represented by given exterior skull mesh boundary surface location 510a).

Computed surface normal 510b may be a computed surface normal at the given exterior skull surface location. Interior skull mesh boundary surface location 520 may represent a location on the interior surface of the patient's skull that intersects a downwards projection from computed surface normal 510b.

As described above, the given exterior skull surface location (represented by given exterior skull mesh boundary surface location 510a) may be a prospective entry point for entering the patient's skull through a cylindrical hole (actual or prospective) having a longitudinal axis along computed surface 510b. As depicted, such a cylindrical hole may have a radius (R) and a computed thickness (T). Here, the computed thickness (T) of the cylindrical hole may be the thickness of the patient's skull along the downwards projection from computed surface normal 510b.

As described above, the distal tip of a targeting cannula for a skull-mounted stereotactic frame may be located approximately at the given exterior skull surface location (represented by given exterior skull mesh boundary surface location 510a). Accordingly, for a skull-mounted stereotactic frame, maximum acceptable angle 510c may represent the maximum acceptable angle for inserting a surgical instrument through the cylindrical hole such that the surgical instrument does not collide with the patient's skull. As discussed above, maximum acceptable angle 510c may have a vertex at given exterior skull mesh boundary surface location 510a (which may represent the distal tip of the targeting cannula for the skull-mounted stereotactic frame).

For the skull-mounted stereotactic frame, examples may compute maximum acceptable angle 510c for a prospective trajectory 570 as follows where a is the maximum acceptable angle, T is the computed thickness of the cylindrical hole, and R is the radius of the cylindrical hole:

$$\tan(\alpha) = \frac{R}{T}$$

As will be described in conjunction with FIG. 6, the computation for the above described maximum acceptable angle may be adjusted for scalp-mounted stereotactic frames where there is a vertical offset between the distal tip of the targeting cannula of the scalp-mounted stereotactic frame and the exterior skull surface of the patient.

Figure 6:
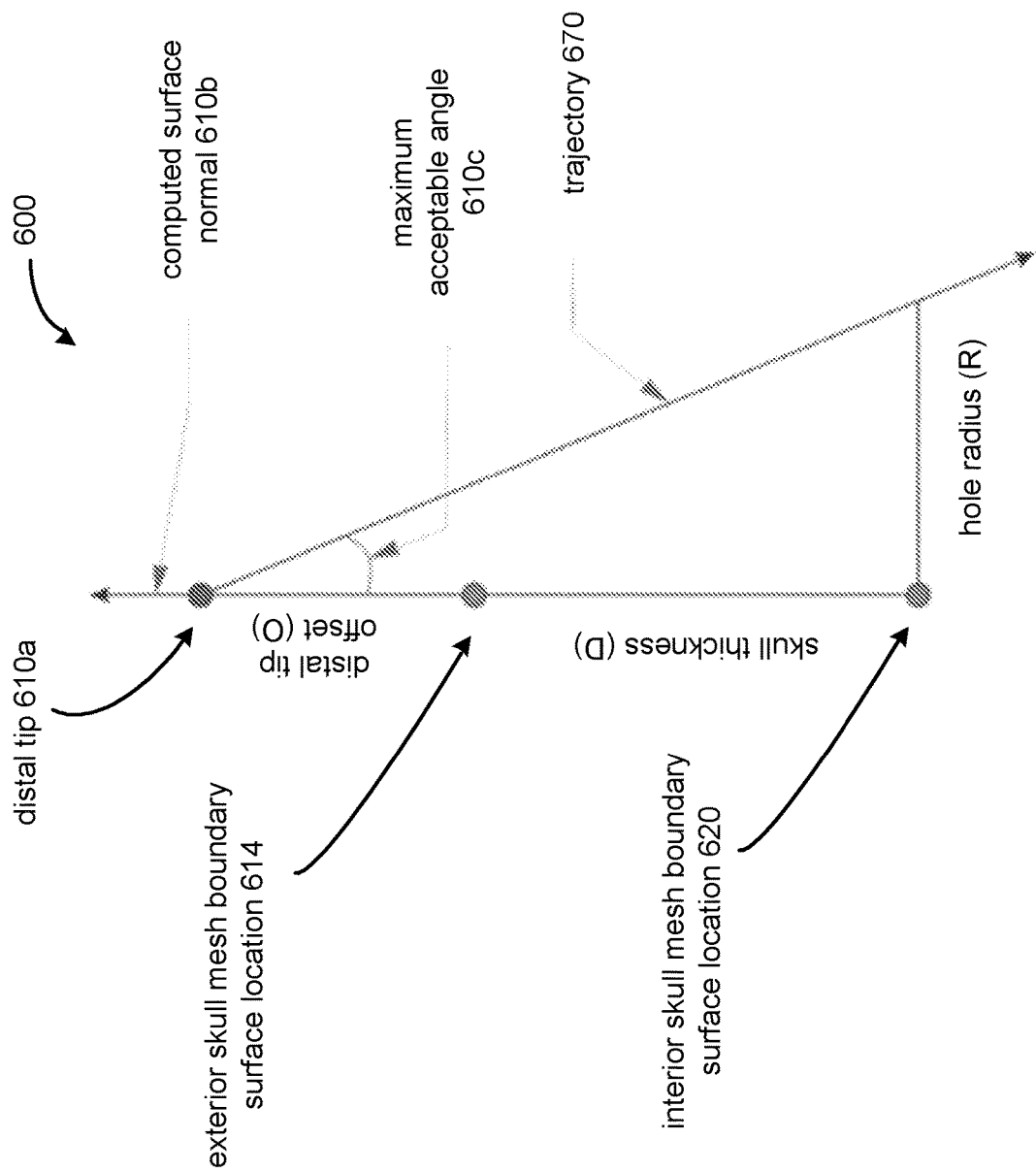
FIG. 6 contains a diagram that depicts how a maximum acceptable angle that avoids bone collision may be computed for a scalp-mounted stereotactic frame, in accordance with various examples of the presently disclosed technology.

FIG. 6 contains a diagram 600 that depicts how a maximum acceptable angle 610c that avoids bone collision may be computed for a scalp-mounted stereotactic frame, in accordance with various examples of the presently disclosed technology. In particular, diagram 600 depicts how examples of the presently disclosed technology may compute maximum acceptable angle 610c for a scalp-mounted stereotactic frame. Components of FIG. 6 having reference numbers corresponding to component reference numbers of components introduced and described above with respect to FIGS. 3-5 may have similar functionality and aspects.

Referring now to diagram 600, distal tip 610a may represent the distal tip of the targeting cannula of the scalp-mounted stereotactic frame. As described above, the distal tip of the targeting cannula for a scalp-mounted stereotactic frame may be located a vertical distance (O) above the exterior skull surface of the patient. As described above, examples may compute a surface normal at the distal tip of the targeting cannula by computing a surface normal at a determined location on an exterior skull mesh boundary surface that corresponds to the distal tip of the targeting cannula, the exterior skull mesh boundary surface representing the patient's exterior skull surface. Examples may determine the location on the exterior skull mesh boundary surface that corresponds to the distal tip of the targeting cannula by: (1) determining the vertical distance (O) that the distal tip of the targeting cannula is located above the patient's exterior skull surface; (2) projecting the exterior skull mesh boundary surface upwards by the determined vertical distance such that the distal tip of the targeting cannula intersects the exterior skull mesh boundary surface; and (3) based on the projection, determining the location on the exterior skull mesh boundary surface that corresponds to the distal tip of the targeting cannula. As depicted, exterior skull mesh boundary surface location 614 may be the determined location on the exterior skull mesh boundary surface that corresponds to distal tip 610a.

Computed surface normal 610b may be a surface normal computed at distal tip 610a. Interior skull mesh boundary surface location 620 may represent a location on the interior surface of the patient's skull that intersects a downwards projection of computed surface normal 610b.

As described above, trajectory 670 may be a prospective trajectory for entering the patient's skull through a cylindrical hole (actual or prospective) having a longitudinal axis along computed surface 610b, the prospective trajectory originating at the distal tip of the targeting cannula. As depicted, such a cylindrical hole may have a radius (R) and a computed thickness (T). Here, the computed thickness (T) of the cylindrical hole may be the thickness of the patient's skull along the downwards projection of computed surface normal 610b.

As described above, distal tip 610a for the scalp-mounted stereotactic frame may be located the vertical distance (O) above the exterior surface of the patient's skull. Accordingly, for the scalp-mounted stereotactic frame, the maximum acceptable angle 610c may represent the maximum acceptable angle for inserting a surgical instrument through the cylindrical hole such that the surgical instrument does not collide with the patient's skull. As discussed above, maximum acceptable angle 610c may have a vertex at distal tip 610a.

For the scalp-mounted stereotactic frame, examples may compute maximum acceptable angle 610c as follows where α is the maximum acceptable angle, T is the computed thickness of the cylindrical hole, O is the distal tip offset, and R is the radius of the cylindrical hole:

$$\tan(\alpha) = \frac{R}{D + O}$$

Figure 7:
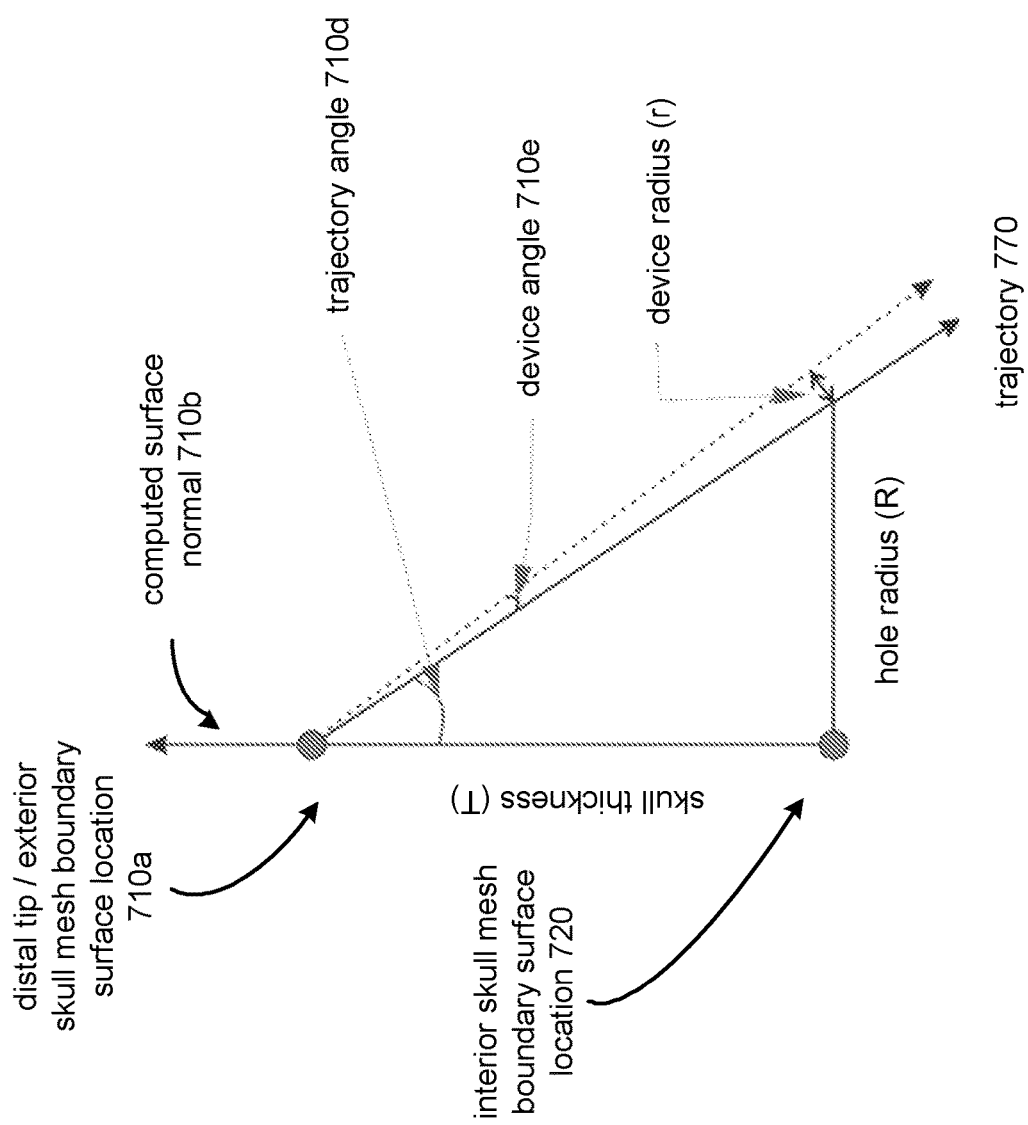
FIG. 7 contains a diagram that depicts how examples of the presently disclosed technology may account for thickness of a surgical instrument when predicting whether a prospective trajectory will collide with a patient's skull, in accordance with various examples of the presently disclosed technology.

FIG. 7 contains a diagram 700 that depicts how examples of the presently disclosed technology may account for a thickness of a surgical instrument when predicting whether a prospective trajectory will collide with a patient's skull, in accordance with various examples of the presently disclosed technology. Components of FIG. 7 having reference numbers corresponding to component reference numbers of components introduced and described above with respect to FIG. 5, may have similar functionality and aspects.

As alluded to above, the surgical instrument inserted through the cylindrical hole in the patient's skull will typically have some thickness/radius. Examples can account for surgical instrument thickness when predicting whether a prospective trajectory will collide with a patient's skull by (1) summing a device angle 710e and a prospective trajectory angle 710d; and (2) determining whether the summed device angle 710e and prospective trajectory angle 710d exceed a computed maximum acceptable angle (here, the maximum acceptable angle may be computed using the techniques described in conjunction with FIGS. 4-6).

Examples may compute the device angle 710e as follows where (A) is the device angle, (r) is the device radius, (T) is the thickness of the cylindrical hole in the patient's skull, and (R) is the radius of the cylindrical hole:

$$\tan(\lambda) = \frac{\text{device radius}}{\sqrt{R^2 + T^2}}$$

Figure 8:
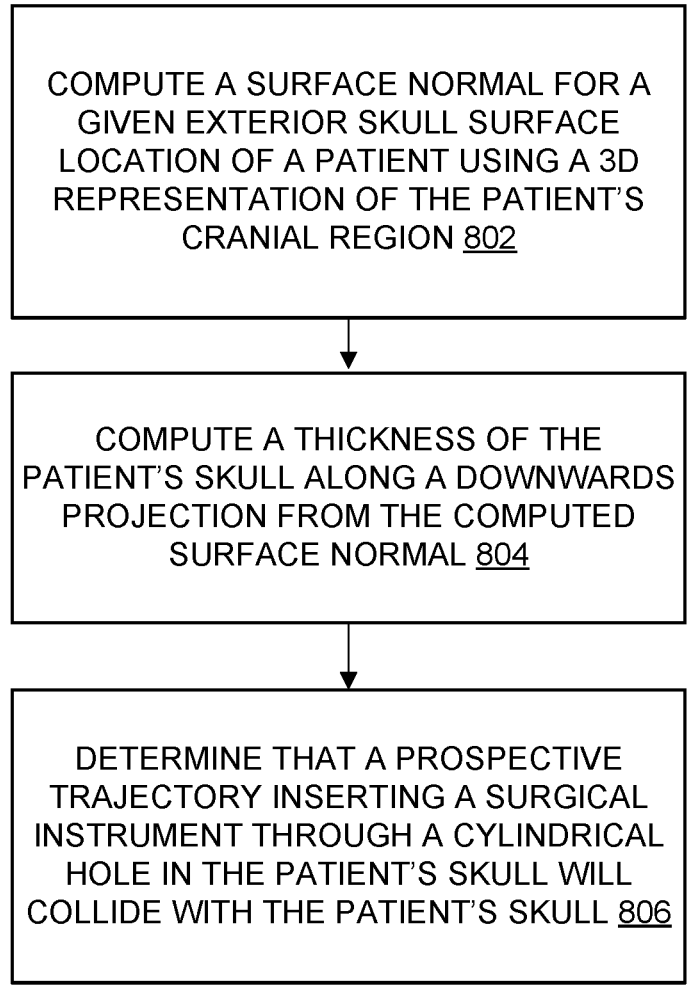
FIG. 8 depicts an example flow diagram that may be used to predict that a prospective trajectory for inserting a surgical instrument through a prospective cylindrical hole in a patient's skull will collide with the patient's skull, in accordance with various examples of the presently disclosed technology.

FIG. 8 depicts an example flow diagram that may be used to predict that a prospective trajectory for inserting a surgical instrument through a prospective cylindrical hole in a patient's skull will collide with a patient's skull, in accordance with various examples of the presently disclosed technology. In various examples, the operations of this flow diagram may be implemented using example-computing component 1100 described in conjunction with FIG. 11.

At operation 802, examples may compute a surface normal to the given exterior skull surface location of the patient using a 3D representation of the patient's cranial region adapted from imaging data of the patient's cranial region.

The given exterior skull surface location may be a prospective entry point for entering the patient's skull through a prospective cylindrical hole having a given radius and a longitudinal axis along the computed surface normal.

The surface normal to the given exterior skull surface location may be a vector perpendicular to the patient's exterior skull surface at the given exterior skull surface location.

The 3D representation of the patient's cranial region may be a 3D representation of the patient's scalp, skull, and brain adapted from imaging data of the patient's cranial region. The imaging data of the patient's cranial region may comprise various types of imaging data including MRI and CT data.

The 3D representation of the patient's cranial region may comprise an exterior skull mesh boundary surface that represents the exterior surface of the patient's skull and an interior skull mesh boundary surface that represents the interior surface of the patient's skull. The exterior and interior skull mesh boundary surfaces may be comprised of mesh elements and mesh vertices.

Examples may compute the surface normal to the given exterior skull surface location using the exterior skull mesh boundary surface. For instance, examples can compute an average of surface normals for one or more mesh elements in close proximity to a location on the exterior skull mesh boundary surface corresponding to the given exterior skull surface location. Alternatively, examples may compute the surface normal to the given exterior skull surface location by performing principal component analysis on one or more mesh vertices in close proximity to the location on the exterior skull mesh boundary surface corresponding to the given exterior skull surface location.

At operation 804, examples may compute a thickness of the patient's skull along a downwards projection from the computed surface normal using the 3D representation. In various examples, this may comprise computing a distance between the location on the exterior skull mesh boundary surface corresponding to the given exterior skull surface location and a location on the interior skull mesh boundary surface that intersects the downwards projection from the computed surface normal.

At operation 806, examples may predict that a prospective trajectory for inserting a surgical instrument through the prospective cylindrical hole will collide with the patient's skull. Here, the prospective trajectory may originate at the given exterior skull surface location.

Examples may predict that the prospective trajectory will collide with the patient's skull based on (a) the computed thickness of the patient's skull; and (b) the given radius of the prospective cylindrical hole. In various examples, this prediction may comprise (1) computing, based on the computed thickness of the patient's skull and the given radius of the prospective cylindrical hole, a maximum acceptable angle for inserting the surgical instrument through the prospective cylindrical hole such that the surgical instrument does not collide with the patient's skull, the maximum acceptable angle having a vertex at the given exterior skull surface location; and (2) predicting that the prospective trajectory creates a prospective trajectory angle that exceeds the maximum acceptable angle, the prospective trajectory angle having a vertex at the given exterior skull surface location.

In various examples, upon predicting that the prospective trajectory will collide with the patient's skull, examples may provide an alert to a clinician, or in certain instances, propose a new trajectory with a new prospective entry point for entering the patient's skull.

Figure 9:
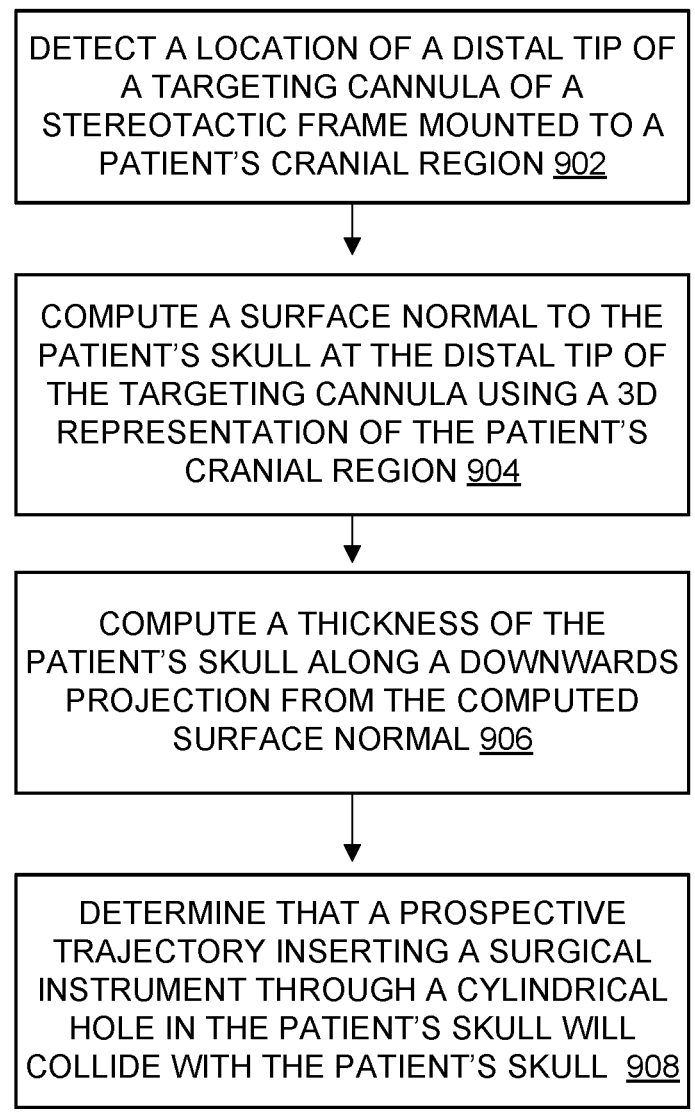
FIG. 9 depicts another example flow diagram that may be used to predict that a prospective trajectory for inserting a surgical instrument through a cylindrical hole in a patient's skull will collide with the patient's skull, in accordance with various examples of the presently disclosed technology.

FIG. 9 depicts another example flow diagram that may be used to predict that a prospective trajectory for inserting a surgical instrument through a cylindrical hole in a patient's skull will collide with the patient's skull, in accordance with various examples of the presently disclosed technology. In various examples, the operations of this flow diagram may be implemented using example-computing component 1100 described in conjunction with FIG. 11.

At operation 902, examples may detect a location of a distal tip of a targeting cannula of a stereotactic frame mounted to a patient's cranial region. In various instances, examples may utilize imaging data from the procedure to detect the location of the distal tip of the targeting cannula.

In some instances, examples may also detect an angulation of the targeting cannula (by e.g., examining imagining data of the procedure). Here, based on the detected location of the distal tip and the detected angulation for the targeting cannula, examples may predict/anticipate the prospective trajectory (as described above, a surgical trajectory can be thought of as originating at the distal tip of the targeting cannula, and proceeding linearly at the angulation of the targeting cannula).

At operation 904, examples may compute a surface normal to the patient's skull at the distal tip of the targeting cannula using a 3D representation of the patient's cranial region adapted from imaging data of the patient's cranial region. As described above, the 3D representation may comprise an exterior skull mesh boundary surface that represents the exterior surface of the patient's skull and an interior skull mesh boundary surface that represents the interior surface of the patient's skull. Accordingly, in various examples, computing the surface normal to the patient's skull at the distal tip of the targeting cannula may comprise (1) determining a location on the exterior skull mesh boundary surface that corresponds to the distal tip of the targeting cannula; and (2) either (a) computing an average of surface normals for one or more mesh elements in close proximity to the determined location on the exterior skull mesh boundary surface corresponding to the distal tip of the targeting cannula; or (b) performing principal component analysis on one or more mesh vertices in close proximity to the location on the exterior skull mesh boundary surface corresponding to the distal tip of the targeting cannula.

Examples may determine the location on the exterior skull mesh boundary surface corresponding to the distal tip of the targeting cannula in various ways depending on whether the stereotactic frame is mounted to the patient's skull (i.e., a skull mount) or scalp (i.e., a scalp mount). Where the stereotactic frame is mounted to the patient's skull, the distal tip of the targeting cannula may be positioned (approximately) at the exterior surface of the patient's skull. Accordingly, the location on the exterior skull mesh boundary surface that corresponds to the distal tip of the targeting cannula may be the location on the exterior skull mesh boundary surface that corresponds to the location on the exterior surface of the patient's skull at which the distal tip of the targeting cannula is positioned. By contrast, where the stereotactic frame is mounted to the patient's scalp, the distal tip of the targeting cannula may be positioned above the exterior surface of the patient's skull by a vertical distance (i.e., a vertical offset). To account for the vertical offset of scalp-mounted stereotactic frames, examples may determine the location on the exterior skull mesh boundary surface that corresponds to the distal tip of the targeting cannula by (1) determining a vertical distance that the distal tip of the targeting cannula is located above the exterior surface of the patient's skull; and (2) projecting the exterior skull mesh boundary surface vertically upwards by the determined vertical distance such that the projection of the exterior skull mesh boundary surface intersects the distal tip of the targeting cannula; and (3) based on the projection, determining the location on the exterior skull mesh boundary surface that corresponds to the distal tip of the targeting cannula.

At operation 906, examples may compute a thickness of the patient's skull along a downwards projection from the computed surface normal using the 3D representation. In various examples, this may comprise computing a distance between the location on the exterior skull mesh boundary surface corresponding to the distal tip of the targeting cannula and a location on the interior skull mesh boundary surface that intersects the downwards projection of the computed surface normal.

At operation 908, examples may predict whether a prospective trajectory for inserting a surgical instrument through a cylindrical hole in the patient's skull will collide with the patient's skull. The prospective trajectory may originate at the distal tip of the targeting cannula, and follow the angulation of the targeting cannula. As described above, in certain instances, examples may predict the prospective trajectory based on the detected location of the distal tip and a detected angulation of the targeting cannula.

The cylindrical hole may have a given radius and a longitudinal axis along the computed surface normal. The cylindrical hole may be a prospective cylindrical hole or a cylindrical hole that has already been drilled/burred into the patient's skull.

The predicting may be based on: (a) the computed thickness of the patient's skull; and (b) the given radius of the cylindrical hole. In various instances, predicting whether the prospective trajectory for inserting the surgical instrument through the cylindrical hole will collide with the patient's skull may comprise: (1) computing a maximum acceptable angle for inserting the surgical instrument through the cylindrical hole such that the surgical instrument does not collide with the patient's skull, the maximum acceptable angle having a vertex at the distal tip of the targeting cannula, the computation of the maximum acceptable angle being based on: (a) the computed thickness of the patient's skull, (b) the determined vertical distance that the distal tip of the targeting cannula is located above the exterior surface of the patient's skull, and (c) the radius of the cylindrical hole; and (2) predicting that the prospective trajectory creates a prospective trajectory angle that exceeds the maximum acceptable angle, the prospective trajectory angle having a vertex at the distal tip of the targeting cannula.

Where the stereotactic frame is mounted to the patient's skull (i.e., where there is no vertical offset between the distal tip of the targeting cannula and the exterior skull surface of the patient), examples may compute the maximum acceptable angle $\alpha$s follows where "$\alpha$" is the maximum acceptable angle:

$$\tan(\alpha) = \frac{\text{cylindrical hole radius}}{\text{computed skull thickness}}$$

Where the stereotactic frame is mounted to the patient's scalp (i.e., where there is a vertical offset between the distal tip of the targeting cannula and the exterior skull surface of the patient), examples may compute the maximum acceptable angle as follows where "$\alpha$" is the maximum acceptable angle and the "distal tip offset" is the determined vertical distance between the distal tip of the targeting cannula and the patient's exterior skull surface (in some cases, this vertical distance may be approximately the thickness of the patient's scalp beneath the distal tip of the targeting cannula):

$$\tan(\alpha) = \frac{\text{cylindrical hole radius}}{\text{computed skull thickness} + \text{pivot offset}}$$

Figure 10:
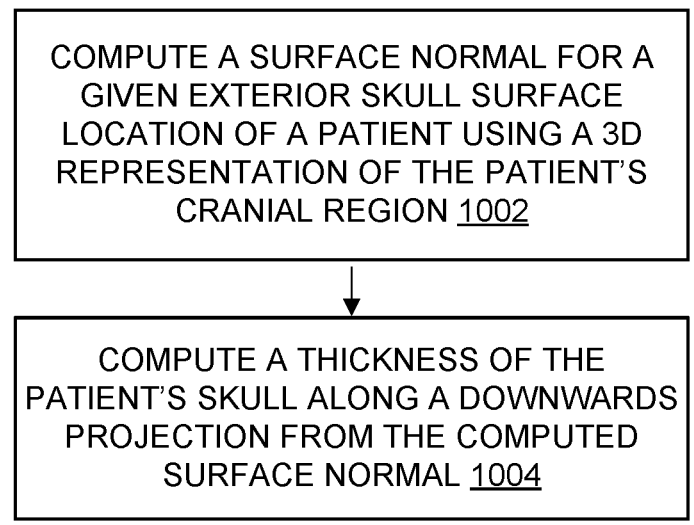
FIG. 10 depicts an example flow diagram that may be used to compute thickness of a patient's skull, in accordance with various examples of the presently disclosed technology.

FIG. 10 depicts another example flow diagram that may be used to compute the thickness of a patient's skull, in accordance with various examples of the presently disclosed technology. In various examples, the operations of this flow diagram may be implemented using example-computing component 1100 described in conjunction with FIG. 11.

At operation 1002, examples may compute a surface normal to a given exterior skull surface location of a patient using a 3D representation of the patient's cranial region adapted from imaging data (e.g., MRI data or CT data) of the patient's cranial region. The 3D representation of the patient's cranial region may comprise an exterior skull mesh boundary surface that represents the exterior surface of the patient's skull and an interior skull mesh boundary surface that represents the interior surface of the patient's skull. The exterior and interior skull mesh boundary surfaces may comprise mesh elements and mesh vertices.

Examples may compute the surface normal to the given exterior skull surface location using the exterior skull mesh boundary surface. For instance, examples can compute an average of surface normals for one or more mesh elements in close proximity to a location on the exterior skull mesh boundary surface corresponding to the given exterior skull surface location. Alternatively, examples may compute the surface normal to the given exterior skull surface location by performing principal component analysis on one or more mesh vertices in close proximity to the location on the exterior skull mesh boundary surface corresponding to the given exterior skull surface location.

At operation 1004, examples may compute the thickness of the patient's skull along a downwards projection from the computed surface normal using the 3D representation. This computation may comprise computing a distance between a location on the exterior skull mesh boundary surface corresponding to the given exterior skull surface location and a location on the interior skull mesh boundary surface that intersects the downwards projection from the surface normal to the given exterior skull surface location.

It should be understood that the techniques described in conjunction with FIG. 10 may be extended for computing scalp thicknesses. For example, the exterior skull mesh boundary surface may instead be an exterior scalp mesh boundary surface representing the patient's exterior scalp surface, the interior skull mesh boundary surface may instead be an interior scalp mesh boundary surface representing the patient's interior scalp surface, and the given exterior skull surface location may be a given exterior scalp surface location. Accordingly, examples may compute surface normals and scalp thickness at the given exterior scalp surface location using the same/similar techniques described above.

Figure 11:
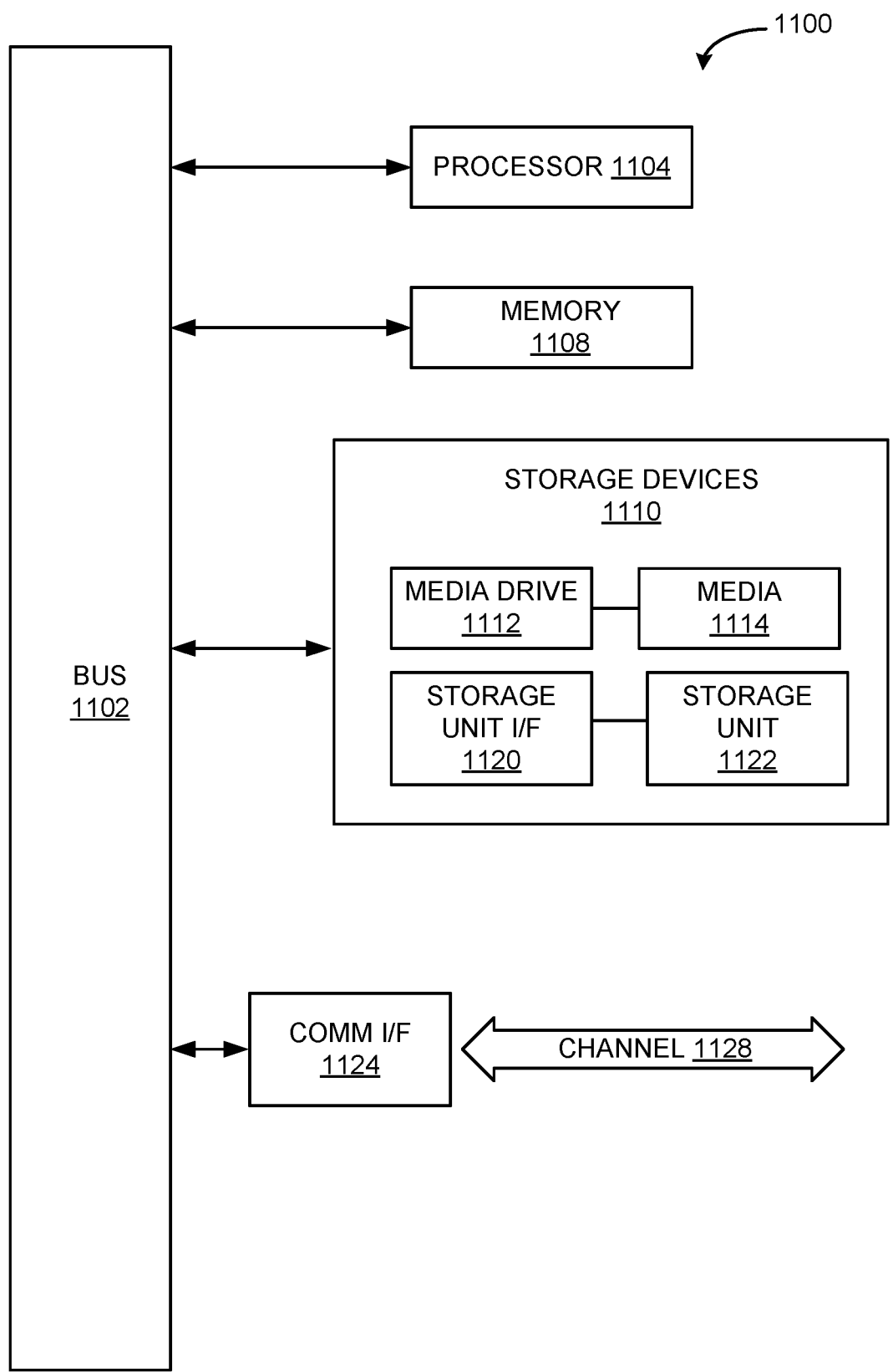
FIG. 11 is an example computing component that may be used to implement various features of examples described in the present disclosure.

As used herein, the terms circuit and component might describe a given unit of functionality that can be performed in accordance with one or more examples of the present application. As used herein, a component might be implemented utilizing any form of hardware, software, or a combination thereof. For example, one or more processors, controllers, ASICs, PLAs, PALs, CPLDs, FPGAs, logical components, software routines or other mechanisms might be implemented to make up a component. Various components described herein may be implemented as discrete components or described functions and features can be shared in part or in total among one or more components. In other words, as would be apparent to one of ordinary skill in the art after reading this description, the various features and functionality described herein may be implemented in any given application. They can be implemented in one or more separate or shared components in various combinations and permutations. Although various features or functional elements may be individually described or claimed as separate components, it should be understood that these features/functionality can be shared among one or more common software and hardware elements. Such a description shall not require or imply that separate hardware or software components are used to implement such features or functionality.

Where components are implemented in whole or in part using software, these software elements can be implemented to operate with a computing or processing component capable of carrying out the functionality described with respect thereto. One such example computing component is shown in FIG. 11. Various examples are described in terms of this example-computing component 1100. After reading this description, it will become apparent to a person skilled in the relevant art how to implement the application using other computing components or architectures.

Referring now to FIG. 11, computing component 1100 may represent, for example, computing or processing capabilities found within a self-adjusting display, desktop, laptop, notebook, and tablet computers. They may be found in hand-held computing devices (tablets, PDA's, smart phones, cell phones, palmtops, etc.). They may be found in workstations or other devices with displays, servers, or any other type of special-purpose or general-purpose computing devices as may be desirable or appropriate for a given application or environment. Computing component 1100 might also represent computing capabilities embedded within or otherwise available to a given device. For example, a computing component might be found in other electronic devices such as, for example, portable computing devices, and other electronic devices that might include some form of processing capability.

Computing component 1100 might include, for example, one or more processors, controllers, control components, or other processing devices. Processor 1104 might be implemented using a general-purpose or special-purpose processing engine such as, for example, a microprocessor, controller, or other control logic. Processor 1104 may be connected to a bus 1102. However, any communication medium can be used to facilitate interaction with other components of computing component 1100 or to communicate externally.

Computing component 1100 might also include one or more memory components, simply referred to herein as main memory 1108. For example, random access memory (RAM) or other dynamic memory, might be used for storing information and instructions to be executed by processor 1104. Main memory 1108 might also be used for storing temporary variables or other intermediate information during execution of instructions to be executed by processor 1104. Computing component 1100 might likewise include a read only memory ("ROM") or other static storage device coupled to bus 1102 for storing static information and instructions for processor 1104.

The computing component 1100 might also include one or more various forms of information storage mechanism 1110, which might include, for example, a media drive 1112 and a storage unit interface 1120. The media drive 1112 might include a drive or other mechanism to support fixed or removable storage media 1114. For example, a hard disk drive, a solid-state drive, a magnetic tape drive, an optical drive, a compact disc (CD) or digital video disc (DVD) drive (R or RW), or other removable or fixed media drive might be provided. Storage media 1114 might include, for example, a hard disk, an integrated circuit assembly, magnetic tape, cartridge, optical disk, a CD or DVD. Storage media 1114 may be any other fixed or removable medium that is read by, written to or accessed by media drive 1112. As these examples illustrate, the storage media 1114 can include a computer usable storage medium having stored therein computer software or data.

In alternative examples, information storage mechanism 1110 might include other similar instrumentalities for allowing computer programs or other instructions or data to be loaded into computing component 1100. Such instrumentalities might include, for example, a fixed or removable storage unit 1122 and an interface 1120. Examples of such storage units 1122 and interfaces 1120 can include a program cartridge and cartridge interface, a removable memory (for example, a flash memory or other removable memory component) and memory slot. Other examples may include a PCMCIA slot and card, and other fixed or removable storage units 1122 and interfaces 1120 that allow software and data to be transferred from storage unit 1122 to computing component 1100.

Computing component 1100 might also include a communications interface 1124. Communications interface 1124 might be used to allow software and data to be transferred between computing component 1100 and external devices. Examples of communications interface 1124 might include a modem or softmodem, a network interface (such as Ethernet, network interface card, IEEE 802.XX or other interface). Other examples include a communications port (such as for example, a USB port, IR port, RS232 port Bluetooth® interface, or other port), or other communications interface. Software/data transferred via communications interface 1124 may be carried on signals, which can be electronic, electromagnetic (which includes optical) or other signals capable of being exchanged by a given communications interface 1124. These signals might be provided to communications interface 1124 via a channel 1128. Channel 1128 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media. Such media may be, e.g., memory 1108, storage unit 1120, media 1114, and channel 1128. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing component 1100 to perform features or functions of the present application as discussed herein.

It should be understood that the various features, aspects and functionality described in one or more of the individual examples are not limited in their applicability to the particular example with which they are described. Instead, they can be applied, alone or in various combinations, to one or more other examples, whether or not such examples are described and whether or not such features are presented as being a part of a described example. Thus, the breadth and scope of the present application should not be limited by any of the above-described exemplary examples.

Terms and phrases used in this document, and variations thereof, unless otherwise expressly stated, should be construed as open ended as opposed to limiting. As examples of the foregoing, the term "including" should be read as meaning "including, without limitation" or the like. The term "example" is used to provide exemplary instances of the item in discussion, not an exhaustive or limiting list thereof. The terms "a" or "an" should be read as meaning "at least one," "one or more" or the like; and adjectives such as "conventional," "traditional," "normal," "standard," "known." Terms of similar meaning should not be construed as limiting the item described to a given time period or to an item available as of a given time. Instead, they should be read to encompass conventional, traditional, normal, or standard technologies that may be available or known now or at any time in the future. Where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "component" does not imply that the aspects or functionality described or claimed as part of the component are all configured in a common package. Indeed, any or all of the various aspects of a component, whether control logic or other components, can be combined in a single package or separately maintained and can further be distributed in multiple groupings or packages or across multiple locations.

Additionally, the various examples set forth herein are described in terms of exemplary block diagrams, flow charts and other illustrations. As will become apparent to one of ordinary skill in the art after reading this document, the illustrated examples and their various alternatives can be implemented without confinement to the illustrated examples. For example, block diagrams and their accompanying description should not be construed as mandating a particular architecture or configuration.

The invention claimed is:

1. A method, comprising:
    computing a surface normal to an exterior skull surface location of a patient using a 3D representation of the patient's cranial region adapted from imaging data of the patient's cranial region, wherein the exterior skull surface location is a prospective entry point for entering the patient's skull through a prospective cylindrical hole having a radius and a longitudinal axis along the computed surface normal to the exterior skull surface location;
    computing, using the 3D representation, a thickness of the patient's skull along a downwards projection from the computed surface normal; and
    predicting, based on the computed thickness and the radius of the prospective cylindrical hole, that a prospective trajectory for inserting a surgical instrument through the prospective cylindrical hole will collide with the patient's skull, the prospective trajectory originating at the exterior skull surface location.

2. The method of claim 1, further comprising, providing an alert that the prospective trajectory will collide with the patient's skull.

3. The method of claim 1, wherein the 3D representation of the patient's cranial region comprises an exterior skull mesh boundary surface that represents the exterior surface of the patient's skull and an interior skull mesh boundary surface that represents the interior surface of the patient's skull, the exterior and interior skull mesh boundary surfaces comprised of mesh elements and mesh vertices.

4. The method of claim 3, wherein computing the surface normal to the exterior skull surface location comprises computing an average of surface normals for one or more mesh elements in close proximity to a location on the exterior skull mesh boundary surface corresponding to the exterior skull surface location.

5. The method of claim 3, wherein computing the surface normal to the exterior skull surface location comprises performing principal component analysis on one or more mesh vertices in close proximity to a location on the exterior skull mesh boundary surface corresponding to the exterior skull surface location.

6. The method of claim 3, wherein computing the thickness of the patient's skull along the downwards projection from the computed surface normal comprises computing a distance between a location on the exterior skull mesh boundary surface corresponding to the exterior skull surface location and a location on the interior skull mesh boundary surface that intersects the downwards projection from the computed surface normal.

7. The method of claim 1, wherein predicting that the prospective trajectory for inserting the surgical instrument through the prospective cylindrical hole will collide with the patient's skull comprises:
    computing, based on the computed thickness of the patient's skull and the radius of the prospective cylindrical hole, a maximum acceptable angle for inserting the surgical instrument through the prospective cylindrical hole such that the surgical instrument does not collide with the patient's skull, the maximum acceptable angle having a vertex at the exterior skull surface location; and
    predicting that the prospective trajectory creates a prospective trajectory angle that exceeds the maximum acceptable angle, the prospective trajectory angle having a vertex at the exterior skull surface location.

8. The method of claim 1 wherein the imaging data of the patient's cranial region comprises at least one of magnetic resonance imaging (MRI) data and computerized tomography (CT) data.

9. Non-transitory computer-readable storage medium including instructions that, when executed by at least one processor of a computing system, cause the computing system to perform a method comprising:
    detecting a location of a distal tip of a targeting cannula of a stereotactic frame mounted to a patient's cranial region;
    computing a surface normal to the patient's skull at the distal tip of the targeting cannula using a 3D representation of the patient's cranial region adapted from imaging data of the patient's cranial region;
    computing, using the 3D representation, a thickness of the patient's skull along a downwards projection from the computed surface normal; and
    predicting that a prospective trajectory for inserting a surgical instrument through a cylindrical hole in the patient's skull will collide with the patient's skull, the prospective trajectory originating at the distal tip of the targeting cannula, the cylindrical hole having a radius and a longitudinal axis along the computed surface normal, wherein the predicting is based on:
        the computed thickness of the patient's skull; and
        the radius of the cylindrical hole.

10. The non-transitory computer-readable medium of claim 9, wherein the method further comprises providing an alert that the prospective trajectory will collide with the patient's skull.

11. The non-transitory computer-readable medium of claim 9, wherein the 3D representation of the patient's cranial region comprises an exterior skull mesh boundary surface that represents the exterior surface of the patient's skull and an interior skull mesh boundary surface that represents the interior surface of the patient's skull, the exterior and interior skull mesh boundary surfaces comprised of mesh elements and mesh vertices.

12. The non-transitory computer-readable medium of claim 11, wherein computing the surface normal to the patient's skull at the distal tip of the targeting cannula comprises:
   determining a location on the exterior skull mesh boundary surface that corresponds to the distal tip of the targeting cannula; and
   computing an average of surface normals for one or more mesh elements in close proximity to the determined location on the exterior skull mesh boundary surface corresponding to the distal tip of the targeting cannula.

13. The non-transitory computer-readable medium of claim 11, wherein computing the surface normal to the patient's skull at the distal tip of the targeting cannula comprises:
   determining a location on the exterior skull mesh boundary surface that corresponds to the distal tip of the targeting cannula; and
   performing principal component analysis on one or more mesh vertices in close proximity to the determined location on the exterior skull mesh boundary surface corresponding to the distal tip of the targeting cannula.

14. The non-transitory computer-readable medium of claim 12, wherein:
   the stereotactic frame mounted to the patient's head is mounted to the patient's scalp; and
   determining the location on the exterior skull mesh boundary surface that corresponds to the distal tip of the targeting cannula comprises:
      determining a vertical distance that the distal tip of the targeting cannula is located above the exterior surface of the patient's skull;
      projecting the exterior skull mesh boundary surface upwards by the determined vertical distance such that the projection of the exterior skull mesh boundary surface intersects the distal tip of the targeting cannula; and
      based on the projection, determining the location on the exterior skull mesh boundary surface that corresponds to the distal tip of the targeting cannula.

15. The non-transitory computer-readable medium of claim 11, wherein computing the thickness of the patient's skull along the downwards projection from the computed surface normal comprises computing a distance between a location on the exterior skull mesh boundary surface corresponding to the distal tip of the targeting cannula and a location on the interior skull mesh boundary surface that intersects the downwards projection from the computed surface normal.

16. The non-transitory computer-readable medium of claim 14, wherein determining that the prospective trajectory for inserting the surgical instrument through the cylindrical hole will collide with the patient's skull comprises:
   computing a maximum acceptable angle for inserting the surgical instrument through the cylindrical hole such that the surgical instrument does not collide with the patient's skull, the maximum acceptable angle having a vertex at the distal tip of the targeting cannula, the computation of the maximum acceptable angle being based on:
      the computed thickness of the patient's skull,
      the determined vertical distance that the distal tip of the targeting cannula is located above the exterior surface of the patient's skull, and
      the radius of the cylindrical hole; and
   predicting that the prospective trajectory creates a prospective trajectory angle that exceeds the maximum acceptable angle, the prospective trajectory angle having a vertex at the distal tip of the targeting cannula.

17. The non-transitory computer-readable medium of claim 9, wherein the imaging data of the patient's skull comprises at least one of MRI data and computerized tomography CT data.

18. The non-transitory computer-readable medium of claim 9, wherein the method further comprises:
   detecting an angulation for the targeting cannula; and
   predicting, based on the detected location of the distal tip of the targeting cannula and the detected angulation of the targeting cannula, the prospective trajectory for inserting the surgical instrument through the cylindrical hole.

19. A system comprising:
   a plurality of processing resources; and
   a non-transitory computer-readable medium, coupled to the plurality of processing resources, having stored therein instructions that when executed by the plurality of processing resources, cause the system to:
      compute a surface normal to an exterior skull surface location of a patient using a 3D representation of the patient's cranial region adapted from imaging data of the patient's cranial region, wherein:
         the 3D representation of the patient's cranial region comprises an exterior skull mesh boundary surface that represents the exterior surface of the patient's skull and an interior skull mesh boundary surface that represents the interior surface of the patient's skull, the exterior and interior skull mesh boundary surfaces comprised of mesh elements and mesh vertices; and
      compute a thickness of the patient's skull along a downwards projection from the computed surface normal using the 3D representation by computing a distance between the location on the exterior skull mesh boundary surface corresponding to the exterior skull surface location and a location on the interior skull mesh boundary surface that intersects the downwards projection from the computed surface normal to the exterior skull surface location.

20. The system of claim 19, wherein computing the surface normal to the exterior skull surface location comprises computing an average of surface normals for one or more mesh elements in close proximity to a location on the exterior skull mesh boundary surface corresponding to the exterior skull surface location.

* * * * *